(12) United States Patent
Karami et al.

(10) Patent No.: US 7,438,709 B2
(45) Date of Patent: Oct. 21, 2008

(54) ABSORBENT ARTICLES HAVING IMPROVED FASTENING SYSTEM

(75) Inventors: Hamzeh Karami, Brewster, MA (US); Kambiz Damaghi, Kings Point, NY (US); Babak Damaghi, Kings Point, NY (US)

(73) Assignee: First Quality Products, Inc., State College, PA (US)

( * ) Notice: Subject to any disclaimer, the term of this patent is extended or adjusted under 35 U.S.C. 154(b) by 0 days.

(21) Appl. No.: 10/470,625

(22) Filed: Feb. 27, 2005

(65) Prior Publication Data

US 2005/0154366 A1 Jul. 14, 2005

Related U.S. Application Data

(63) Continuation of application No. 09/844,726, filed on Apr. 27, 2001, now abandoned, which is a continuation-in-part of application No. 09/797,334, filed on Mar. 1, 2001, now abandoned, which is a continuation-in-part of application No. 09/376,282, filed on Aug. 18, 1999, now abandoned, which is a continuation-in-part of application No. 09/149,265, filed on Sep. 8, 1998, now Pat. No. 6,306,121.

(51) Int. Cl.
*A61F 13/15* (2006.01)

(52) U.S. Cl. .................. 604/389; 604/390; 604/392; 604/396; 604/385.01; 604/385.201

(58) Field of Classification Search .............. 604/389, 604/390, 392, 386, 387, 396, 385.01, 385.201
See application file for complete search history.

(56) References Cited

U.S. PATENT DOCUMENTS

| | | | |
|---|---|---|---|
| 2,493,113 A | 1/1950 | Dance | |
| 4,051,854 A | 10/1977 | Aaron | |
| 4,662,875 A * | 5/1987 | Hirotsu et al. | 604/389 |
| 4,995,873 A | 2/1991 | Knight | |
| 5,135,522 A | 8/1992 | Fahrenkrug et al. | |
| 5,279,604 A | 1/1994 | Robertson et al. | |
| 5,368,585 A | 11/1994 | Dokken | |
| H1440 H | 5/1995 | New et al. | |
| 5,411,498 A | 5/1995 | Fahrenkrug et al. | |
| H1674 H | 8/1997 | Ames et al. | |
| 5,897,545 A | 4/1999 | Kline et al. | |
| 5,904,675 A | 5/1999 | Laux et al. | |
| 5,906,604 A | 5/1999 | Ronnberg et al. | |
| 5,926,926 A | 7/1999 | Kato | |
| 6,306,121 B1 | 10/2001 | Damaghi et al. | |
| 6,626,881 B2 * | 9/2003 | Shingu et al. | 604/385.201 |

FOREIGN PATENT DOCUMENTS

| | | |
|---|---|---|
| EP | 0 528 282 | 2/1993 |
| EP | 1 077 054 | 2/2002 |

OTHER PUBLICATIONS

EP Search Report, published Dec. 15, 2003.

* cited by examiner

*Primary Examiner*—Jacqueline F. Stephens
(74) *Attorney, Agent, or Firm*—Amster, Rothstein & Ebenstein

(57) ABSTRACT

A disposable absorbent article such as, e.g., a T-shaped diaper comprising two portions, a lateral portion (backwaist) having two lateral segments or wings for wrapping around the waist of a wearer of the diaper, and a second vertical portion or insert which is adapted to be passed under the crotch of the wearer and folded thereover. A uniquely designed tape tab located at the outer lateral end of one wing assures more perfect and comfortable fit. Tape tabs are also provided at the distal ends of vertical portion for engagement onto landing zones disposed on the surface of each wing. These tape tabs may have the same general construction as the tape tab on the diaper wing. The dimensions of the diaper and several of its components and the relative locations of these components are important factors which contribute to improved fitness and functions of the diaper.

3 Claims, 16 Drawing Sheets

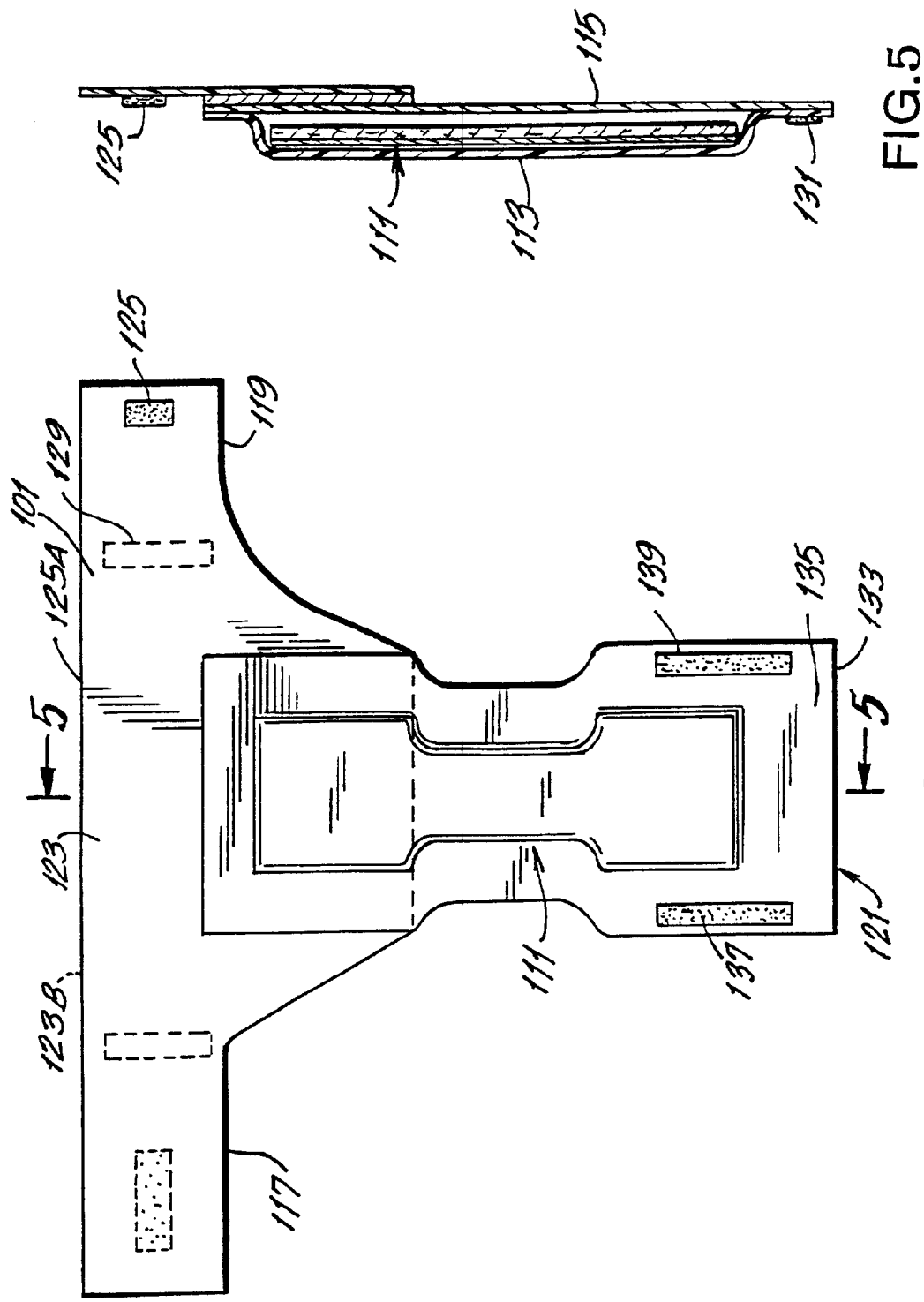

ABSORBENT ARTICLES HAVING IMPROVED FASTENING SYSTEM

RELATED APPLICATIONS

This application is a continuation of application Ser. No. 09/844,726, filed Apr. 27, 2001, which is, in turn, a continuation-in-part of application Ser. No. 09/797,334, filed Mar. 1, 2001, now abandoned, which is, in turn, a continuation-in-part of application Ser. No. 09/376,282, filed Aug. 18, 1999, now abandoned, which is, in turn, a continuation-in-part of application Ser. No. 09/149,265, filed Sep. 8, 1998, now U.S. Pat. No. 6,306,121.

FIELD OF THE INVENTION

The present invention relates to absorbent articles such as disposable diapers, infant and adult incontinent briefs and underpants used for absorption and containment of urine and other body exudates. More particularly, this invention relates to a fastening system used in such articles for providing an improved and effective means of detachably securing the front and rear of such articles. In one particular aspect, this invention relates to providing such fasteners in T-shaped briefs. In another aspect, this invention relates to the dimensions of the brief and several components of the brief as well as the locations of some of the components.

BACKGROUND OF THE INVENTION

The aforementioned copending application Ser. No. 09/376,282 describes an embodiment of the invention therein which is directed to a generally T-shaped brief, e.g., a diaper which comprises a chassis having two intersecting portions which together define a generally T-shaped configuration when the chassis is laid out flat and viewed in stretched position. One of the two portions or pieces is a crosspiece comprising opposed lateral segments or wings adapted to be wrapped on the waist of a wearer of the diaper such as to overlap each other, and the second portion or piece is vertical relative to the crosspiece and has a proximal end, and a distal end which can be passed under the crotch and folded upwardly and over or under the overlapped wings. The T-shaped diaper described in said copending application is provided with a fastening system designed to secure the diaper tightly but comfortably around the waist as illustrated in FIGS. 23-28 of said application. Another variant of the invention, i.e., a generally H-shaped diaper as shown in FIG. 28. The disclosure of said application Ser. No. 09/376,382 is fully incorporated herein by reference.

T-shaped diapers have received widespread attention and acceptance due, in part, to their relative ease of fabrication and use, and the comfort they provide to the wearer as well as the protection they afford against leakage of urine and body exudates. A variety of T-shaped briefs or diapers have been described in the prior art.

For example, one T-shaped diaper was described in U.S. Pat. No. 4,051,854 issued to Gabrielle Leonie Aaron on Oct. 4, 1977. The diaper described therein has a center flap and two ear flaps which, when laid flat, defines a T-shape configuration as shown in FIGS. 1 and 3 of that patent. Fastening means are provided in the form of multiplicity of hooks and loops for fastening the ear flaps to the center flap.

Another T-shaped diaper is described in U.S. Pat. No. 4,995,873 issued to Jacklyn M. Knight on Feb. 26, 1991 which comprises a crosspiece and an intersecting piece which together define the T-shape configuration of the diaper when laid out in flat position. The crosspiece has opposite ends or wings which encircle the waist in an overlapping manner and the intersecting piece passes under the crotch and upwardly and over the crosspiece. Releasable fastening means such as press-on/rip-off adhesive or Velcro.RTM. strips are employed to attach the intersecting piece to the crosspiece.

Whether using a T-shaped diaper or other types of diapers, it is essential that the diaper meet at least two significant criteria, i.e., comfort to the wearer and protection against leakage of body fluids and exudates. In order to achieve these objectives, many prior art workers in the field have focused on providing the diaper with an effective fastening system. Indeed, in the aforementioned application Ser. No. 09/372,382, the inventors describe a fastening system for T-shaped diaper designed to achieve the foregoing objectives. Thus, in the T-shaped diaper described therein, one female fastening means is provided on the lateral wing or segment of the crosspiece and at least one male fastening means is provided on the other lateral wing or segment of the crosspiece such that when the two lateral segments are wrapped around the waist and overlap each other, the male fastener engages the female fastener. In addition, a pair of spaced apart female fasteners are provided on said crosspiece between the end fasteners in the wings such that when the two wings are wrapped around the waist and folded over each other as aforesaid, said two spaced apart female fasteners will be engaged by a pair of spaced apart male fasteners located at the distal end of the vertical piece of the T-shaped diaper.

As it can be seen from the description in the aforementioned application Ser. No. 09/376,382 and the prior art in general, a variety of fasteners are employed such as, e.g., adhesive tape tabs, Velcro.RTM., fabrics which act as female surface for a male fastener, so-called hook and loop fasteners, or even mechanical elements. As it can also be appreciated, the concern over providing a leak-proof, and good fitting diaper is not limited to a particular shaped diaper. Regardless of their shapes, it is essential that the diaper be provided with an effective fastening means which assures tight but comfortable wear, and affords protection against leakage of fluid and body exudates.

Recently, in U.S. Pat. No. 5,906,604 issued on May 25, 1999 to Ronnberg et al., the patentee describes an attachment means for a belt used with an absorbent garment. The belt is either integrated with the absorbent garment, or it can be a separate belt attached to the absorbent garment by means of a releasable attachment such as hook and loop type fastening means, e.g., VELCRO.RTM. Other fastening systems are described in the patents referred to in the aforementioned Ronnberg et al. patent as well as a host of other prior art patents.

A mechanical fastening system for absorbent articles is described in U.S. Pat. No. 5,279,604 issued to Robinson et al. on Jan. 18, 1994. The mechanical fastening system described therein comprises a tape tab having a first fastening element, a landing member comprising a second fastening element which is engageable with the first fastening element, and an additional fastening element for securing the absorbent article in a manner which facilitates disposal of the article.

Notwithstanding the plethora of prior art patents describing a variety of fastening systems for different diapers, there is still a need for a fastening system which is inexpensive, simple to apply to the garment and is effective in preventing leakage of body fluids and exudates from the diaper.

Accordingly, it is an object of the present invention to provide an absorbent article, e.g., a diaper, which has an improved fastening system.

It is also an object of this invention to provide such diaper with a fastening system which is easy to apply to the diaper and which is adjustable to assure comfort and fitness to the body of the wearer, and which can afford maximum protection against leakage of urine and body exudates.

It is another object of this invention to provide a diaper having an improved fastening system wherein the diaper, when laid out flat, has a T-shaped configuration.

It is yet another object of this invention to provide a T-shaped diaper of certain dimensions which has components of defined dimensions and advantageous relative locations.

The foregoing and other features and advantages of the present invention will be appreciated from the following detailed description taken with the accompanying drawings.

SUMMARY OF THE INVENTION

The present invention provides a diaper, such as a T-shaped diaper, having novel fastening system. The T-shaped diaper has a chassis comprising two intersecting portions or cross pieces which define the T-shape configuration of the diaper when viewed in stretched position. One portion is a lateral piece having lateral segments or wings which are adapted to be wrapped around the waist of a wearer of the diaper. The second portion is a vertical piece having a proximal end attached to the chassis and a distal end with tape tabs. The vertical portion is adapted to be passed under the crotch region of the diaper, folded thereover and attached to landing zones on the surface of the lateral segments by the tape tabs located at said distal end.

In order to assure fit and comfort, a novel tape tab is provided at or near one of said segments or wings, e.g., the right segment when the diaper is viewed in front stretched position. Tape tabs are also provided at the distal ends of the intersecting vertical portion which may be similar to the tape tab located on the wing of the diaper.

In accordance with this invention several fastening systems are disclosed which are more fully discussed in the detailed description of the present invention.

The relative dimensions of the wings and the chassis components of the absorbent article, the width of the landing zones and their and location, the relaxed overall dimensions of the chassis are factors which contribute to providing a commercially attractive and easy-to-package brief which fits snugly and comfortably around the body of the wearer.

BRIEF DESCRIPTION OF THE DRAWINGS

In the drawings, wherein like reference numerals are employed to designate like parts wherever possible:

FIG. 4 is a stretched view of the diaper of FIG. 1 when it is laid out flat;

FIG. 5 is a sectional view taken along the line 5-5 of FIG. 4;

DETAILED DESCRIPTION OF THE DIFFERENT EMBODIMENTS OF THE INVENTION

Figure 1:
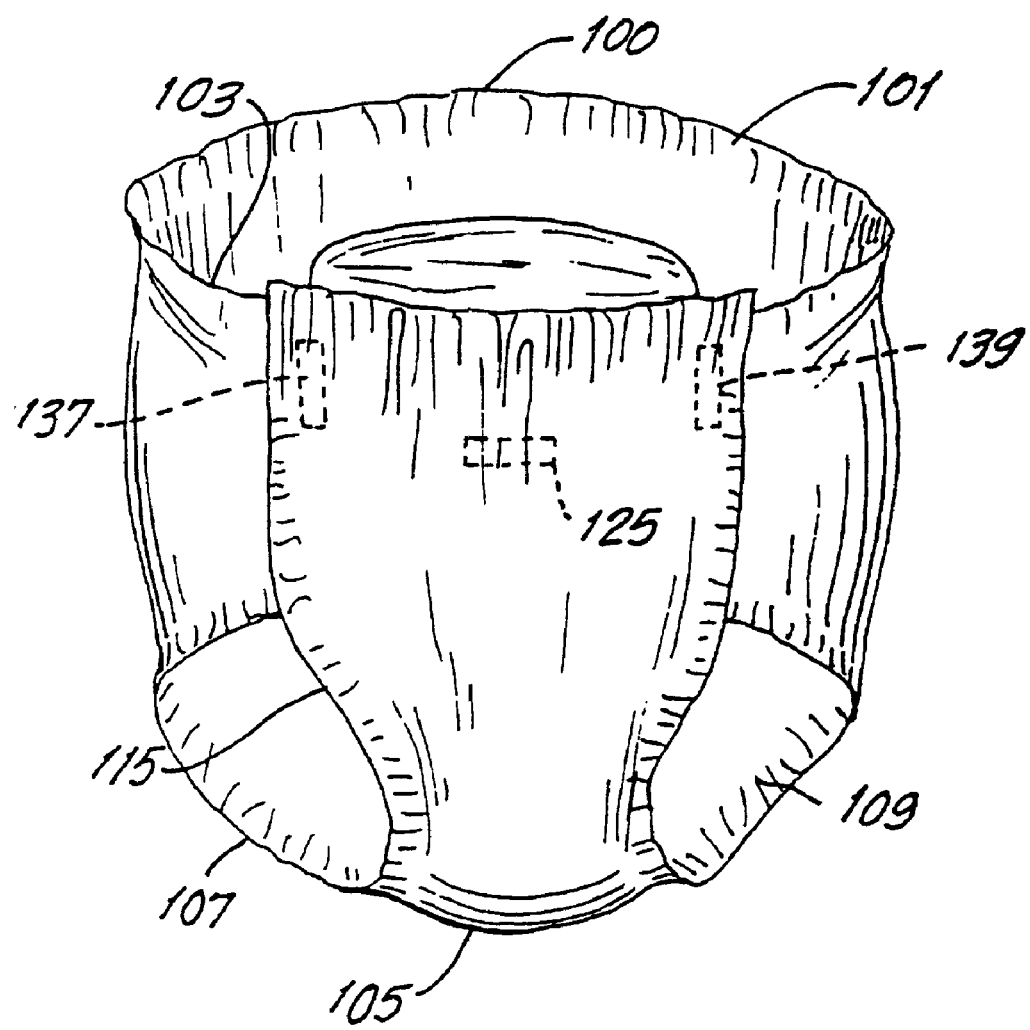
FIG. 1 is a perspective view of a T-shaped diaper in assembled form when worn by a wearer.
Figure 2:
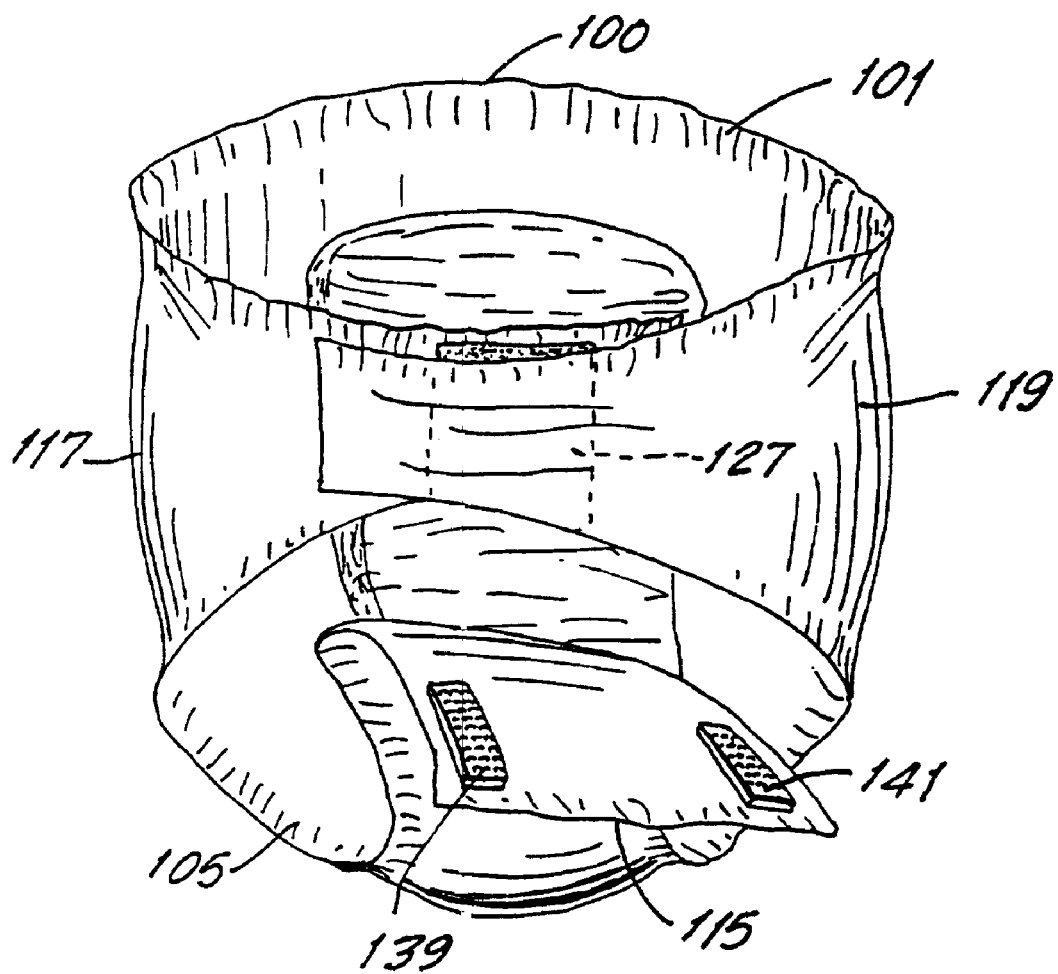
FIG. 2 is perspective view of the diaper in FIG. 1 showing the center vertical segment with its distal end partly folded upward and away from the diaper chassis and showing an insert and a belt attached together.
Figure 3:
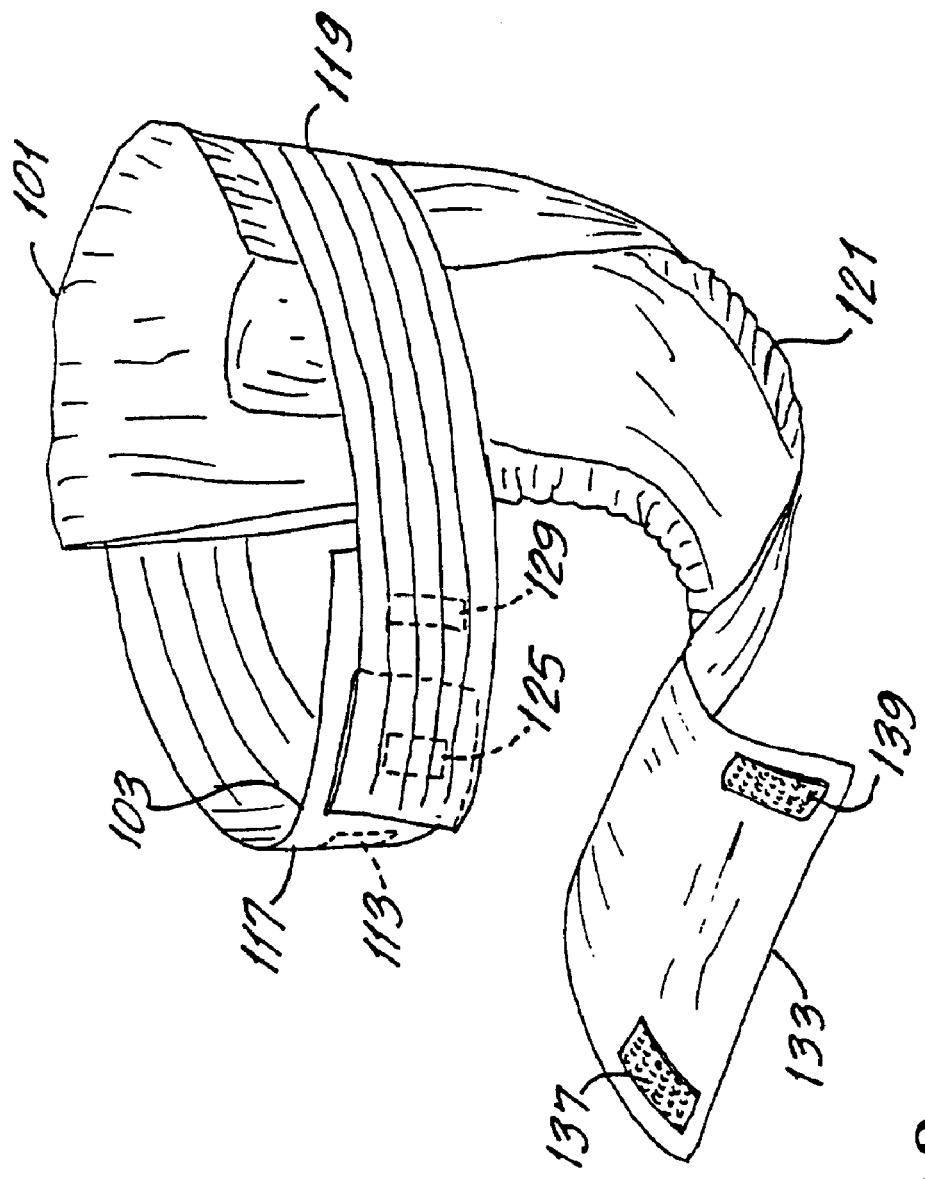
FIG. 3 is another perspective view of the diaper of FIG. 2 but showing the center vertical segment hanging more freely prior to assembling the diaper.

Referring first to FIGS. 1-5, there is shown in FIG. 1, a diaper generally designated as 100 comprising a chassis having a back waist region 101 and a front waist region 103 (which may be elasticized), a crotch region 105 and a pair of leg openings 107,109 through which extend the legs of the wearer. The diaper 100 also comprises an absorbent core or pad 111 which is disposed between a liquid pervious cover sheet 113 and a liquid impervious backsheet 115 as illustrated in FIG. 5 and described hereinafter. The back waist region 101 comprises a mid region 123 having a pair of opposed laterally extending segments or ears 117,119 and a center intersecting segment or flap 121 which extends vertically downward relative to the ears 117,119 as illustrated in FIGS. 2, 3 and 4. The ear segments 117,119 are adapted to be wrapped around the waist, and the center vertical segment 121 is adapted to be passed under the crotch region 105, pulled up and folded over the crotch region and engaged onto the ear segments 117,119 as hereinafter described. In order to assure a more perfect fit of the diaper around the torso of the wearer, the ear segments 117,119 and the center flap 121 are provided with fastening means at strategic locations on their respective surfaces. For example, in the embodiment shown in FIG. 4, the front surface 123A of the mid region 123 is provided with a male Velcro-type fastening means 125 adjacent the right lateral end of the ear segments 119, and the reverse surface 123B opposite the surface 123A is provided with a female Velcro-type fastening means 127,129,131. The distal end 133 of the center segment 121 has a top surface on which is provided a pair of opposed, generally parallel and spaced apart male Velcro-type fastening means 137,139. As it will become apparent from the description of the assembly of the diaper during its use, the fastening means on the ear segments and the center segment are located at such positions as to result in a remarkable tight fit diaper which is highly effective against leakage of fluid and body exudates.

In use, the ear segment 117 is wrapped around the waist first, followed by wrapping the ear segment 119 around the waist to overlap the ear segment 117, and the male Velcro fastener 125 is engaged onto the female Velcro fastener 131. The center segment 121 is then passed under the crotch of the wearer and folded thereover and upwardly onto the top surface 123A of the diaper, and then engaging the male Velcro fasteners 139 and 137 onto the corresponding aligned female Velcro fasteners 127 and 129 respectively. By proper spacings and alignments of the male/female Velcro fasteners, the fasteners will mate, i.e., inter-engage, thus resulting in a more perfect fit to the waist of the wearer and prevent leakage of the body fluids and exudates out of the diaper.

The materials and fabrics used in making the diapers of the present invention are generally of the type and variety known in the art and are described, for example, in U.S. Pat. Nos. 4,695,278 and 4,795,454 and in copending, commonly assigned application Ser. No. 09/149,265, filed Sep. 8, 1998, the disclosures of which are fully incorporated herein by reference. Thus, the liquid pervious cover sheet is a compliant soft material which is skin friendly and does not cause rash or irritation. Such materials include porous foams, reticulated foams, plastics, natural fibers such as woods or cotton fibers, synthetic fibers made of polyester or propylene available from First Quality Fibers, Inc., McElhattan, Pa., or made from a combination of such materials.

The absorbent pad or core may be manufactured from a wide variety of liquid absorbent materials of the type usually used in manufacturing disposable diapers and other absorbent articles. Such materials include comminuted wood pulp, creped cellulose wadding, absorbent foams and sponges, super absorbent polymers, or a combination of said materials.

The acquisition layer is usually made of chemically bonded nonwoven polyester available from American Nonwovens, Columbus, Miss. Preferably, the width of this layer is substantially the same as the width of the crotch absorbent core. This core may be made of wood pulp fibers and super absorbent polymers (SAP) such as IM 7000 series available from Clarian Products, Inc., Portsmouth, Inc., Va., and Chemdal 2000 series, available from Chemdal Inc. Palantine, Ill. Alternatively, the absorbent core may be made of dual layer construction, in which case, the absorbent polymer may be securely positioned between each layer of the absorbent material.

The film backing is usually a polyethylene layer which is liquid, air and preferably vapor impermeable, and is placed under the absorbent core to prevent the body exudates from leaking and otherwise soiling the user's bed and clothing. The width and length of the backing film are generally wider and longer than the width and length of the absorbent core. Polyethylenes suitable as backing film for the purpose of this invention are available from Clopay Plastics, Cincinnati, Ohio. The topsheet is also preferably made of spunbond nonwoven polypropylene and is usually coextensive with the backing film. In general, however, the various layers are of the type and materials well known in the diaper industry and within the scope and knowledge of those versed in this art.

In the T-shaped diaper described and illustrated by reference to FIGS. 1-5, the fastening system employed is the system described in the aforementioned application Ser. No. 09/376,282, the disclosure of which is fully incorporated herein by reference. The ensuing description, however, will be directed to the novel fastening system of the present invention, and will be described in connection with a T-shaped diaper, although it may be employed in other absorbent articles as well.

Figure 8:
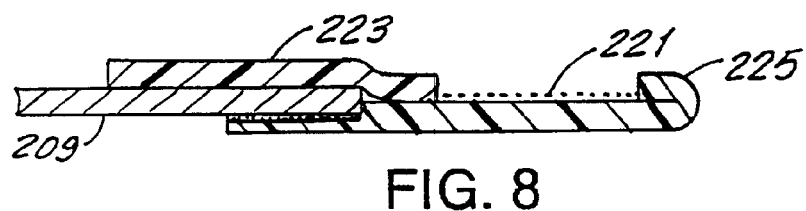
FIG. 8 is a sectional view taken along the line 8-8 of FIG. 7.
Figure 9:
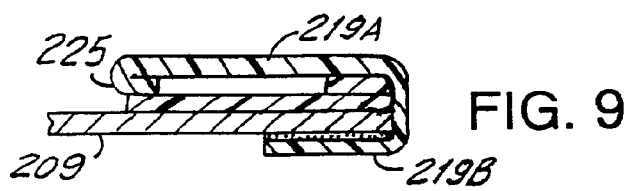
FIG. 9 is a sectional view taken along the line 9-9 of FIG. 6.
Figure 10:
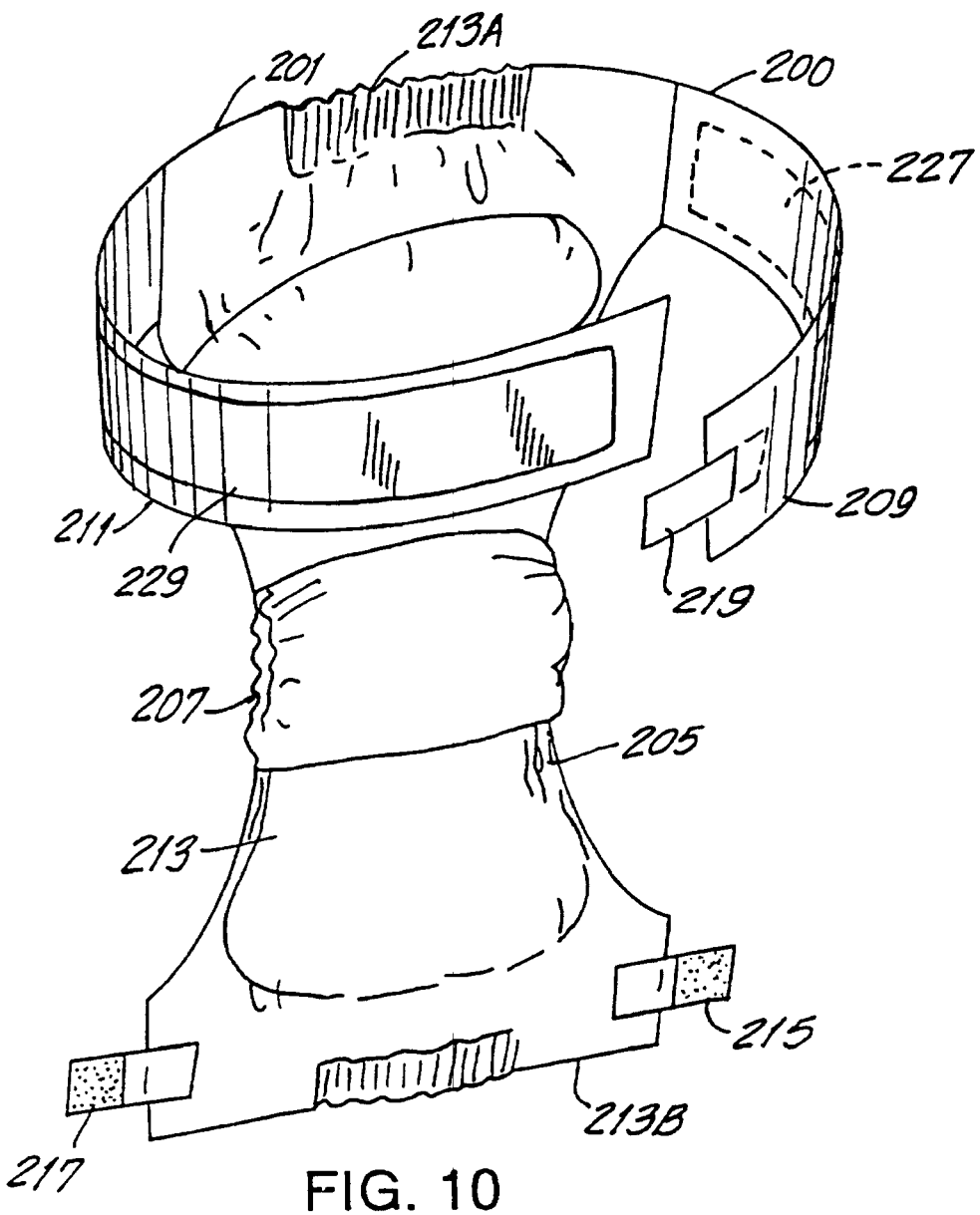
FIG. 10 is a partly perspective view of a diaper having a tape tab and landing zone fastening system ready for use.
Figure 11:
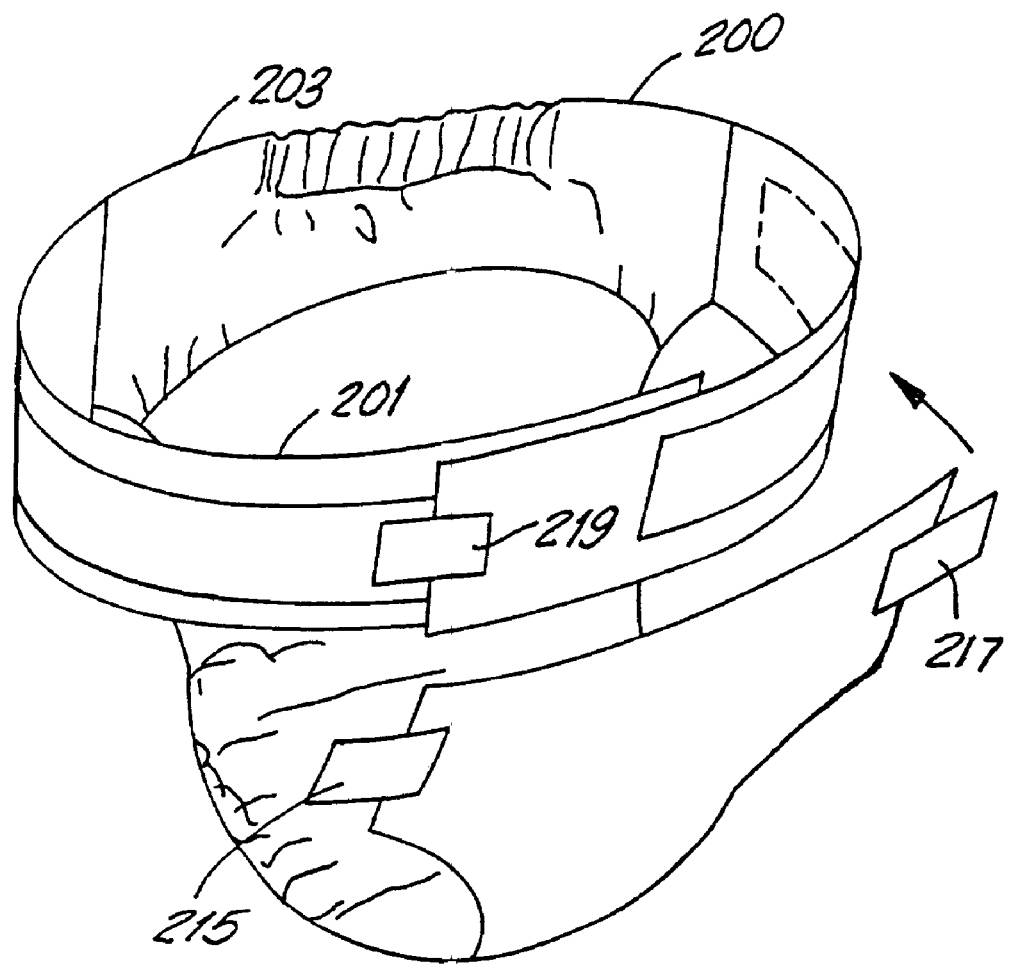
FIG. 11 is a perspective view of the diaper shown in FIG. 10 in ready to be assembled position.

A first embodiment of the fastening system of the present invention is shown in FIGS. 6-9 and a diaper incorporating this fastening system is shown, in perspective view, in FIGS. 10-11. As shown in FIGS. 10 and 11, the diaper generally designated as 200 comprises a chassis having a back waist region 201 a front waist region 203 and a crotch region 205 and an absorbent core 207. A pair of opposed lateral segments or wings 209, 211 extend from the respective edges of the back waist region 201, and a generally vertical intersecting piece 213 having a proximal end 213A attached to the diaper chassis and a distal end 213B with a pair of opposed tapes 215, 217 disposed at each side of the intersecting piece near the distal end thereof.

Figure 6:
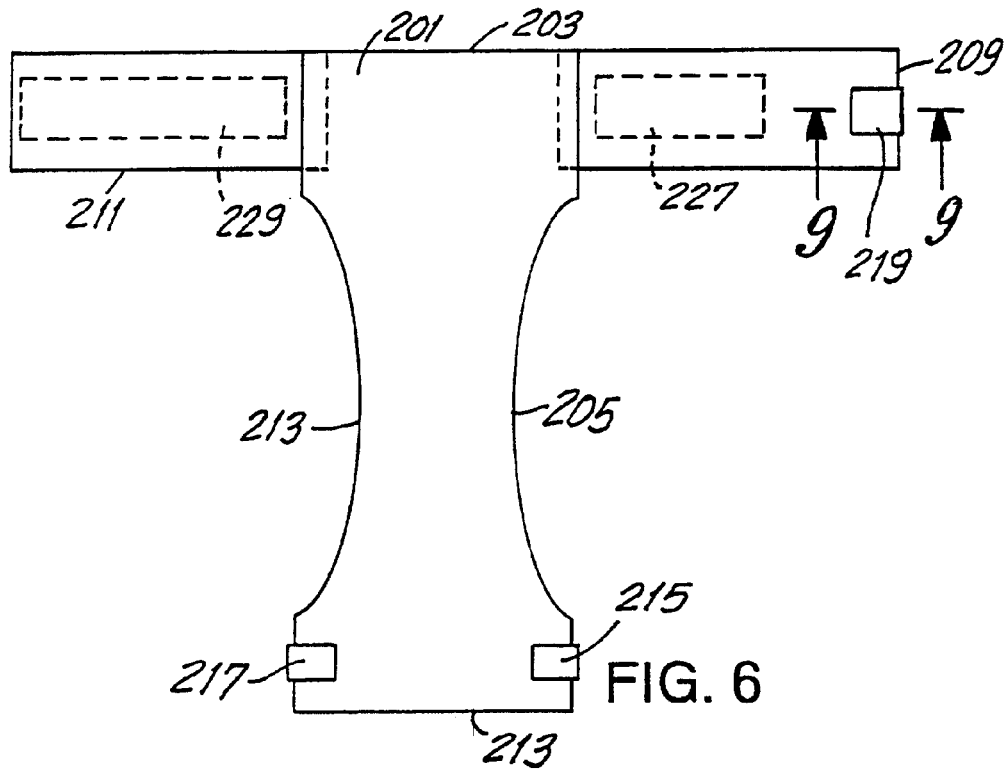
FIG. 6 is a view of a T-shaped diaper in stretched position employing a tape tab and landing zone fastening system according to one embodiment of the present invention.
Figure 7:
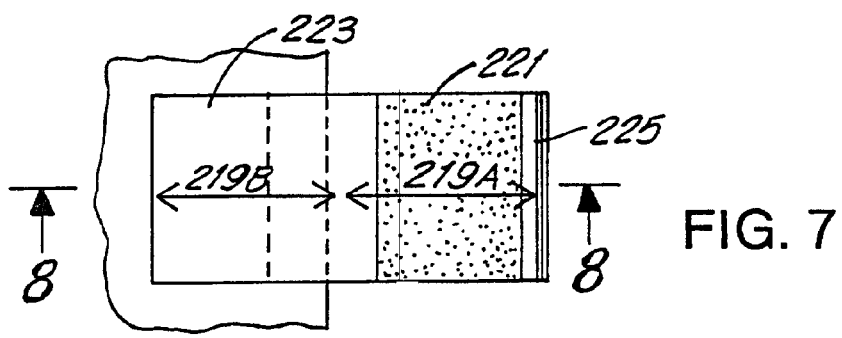
FIG. 7 is a top view of the tape tab shown in FIG. 6, with the fastener tape in open, ready to be used position.

Referring to FIGS. 6-9, there is shown in FIGS. 6 and 7 the tape tab 219 having a portion 219A used to fasten the tape to the diaper, and a second portion 219B permanently attached to the bottom surface of the wing 209, i.e., the surface away from the skin of the wearer (see FIGS. 8 and 9). The tape portion 219 has a top surface 221 covered with a pressure sensitive adhesive, and an opposed bottom surface made of a suitable plastic such as, e.g., polyethylene or polypropylene film, or other material such as, e.g., woven or nonwoven. As shown in FIG. 7, the fastening system of this embodiment comprises a release tape 223 having a top surface coated with a release agent such as a silicone compound, and an opposed bottom adhesive surface with a portion of the release tape 223 attached to the portion 219A and the other portion adhered to the top surface of the wing 209. Before use, the portion 219A is folded over the portion 219B in order to protect the adhesive surface during transportation of the product. For convenience of manipulation, the lateral edge of the tape 219 is folded upon itself so as to form an adhesive-free grip strip (Finger lift) 225.

The other component of the fastening system in this embodiment of the invention are landing zones (tapes) 227, 229 located on the lateral segments or wings 209 and 211, respectively. The size of each landing zone may be varied if desired depending on the size of the diaper. Each landing zone has an outer surface covered, at least partly, with a release agent such as a silicone compound. This allows the tape tab 219 to be positioned and repositioned on the landing zone 229 several times without tearing the diaper fabric.

In use, the tape tabs 219 is peeled away from the tape tab 219A by gripping and pulling away the grip strip 225. The diaper wings 209 and 211 are then wrapped around the waist of the wearer and the pressure sensitive surface 221 of the tape 219 is secured to the landing zone 229. Thereafter, the insert piece 213 is passed under the crotch, folded thereover and the tape tabs 215 and 217 located at the distal end of the insert piece is releasably secured to the landing zones such that tape tab 215 is secured to the landing zone 227 and tape tab 217 is secured to the landing zone 229. Tape tabs 215 and 217 may each have the same construction as tape tab 219, if desired. As it can be seen, the fastening system permits repeated adjustments and repositioning of the tape tabs on the landing zones to achieve a desired fit without tearing the fabric of the diaper.

Figure 12:
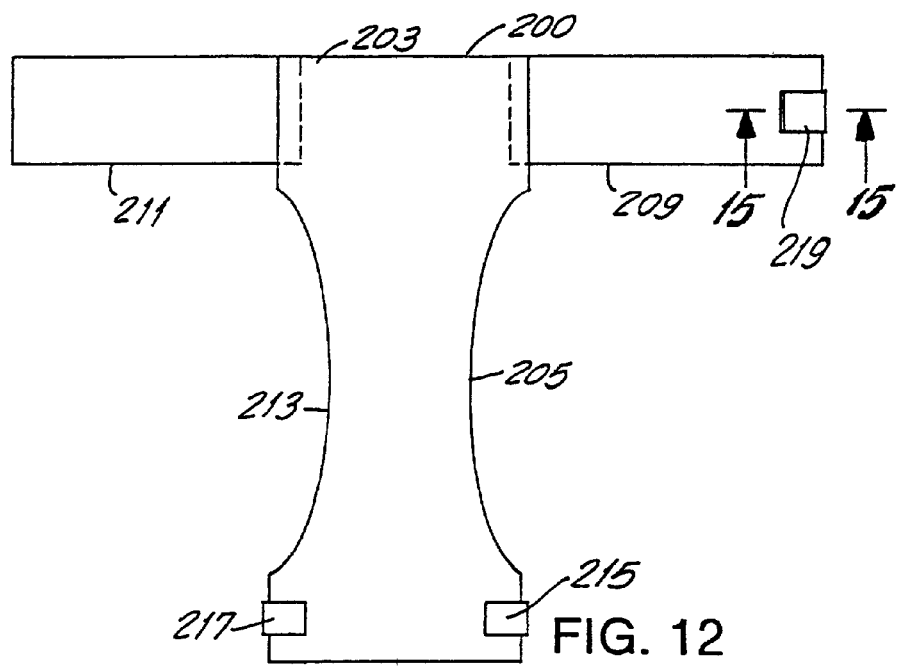
FIG. 12 is a view similar to FIG. 6 employing multi-layer tape tab and landing zone fastening system according to another embodiment of the present invention.
Figure 13:
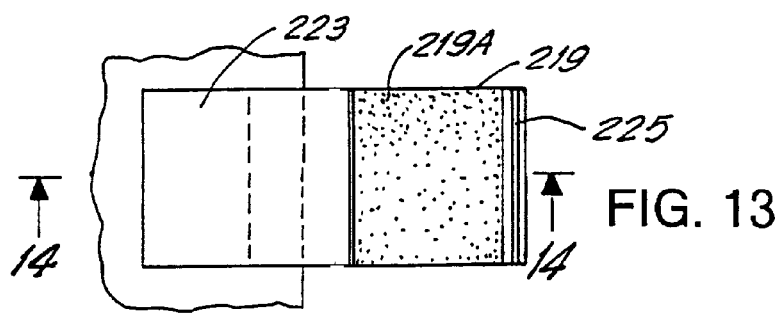
FIG. 13 is a top view of the multi-layer tape tab and landing zone fastening system of FIG. 12 with the fastener tape in open ready to use position.
Figure 14:
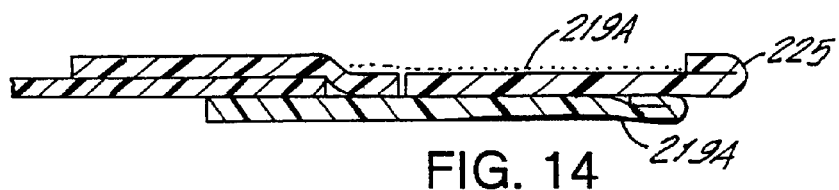
FIG. 14 is a sectional view taken along the line 14-14 of FIG. 13.
Figure 15:
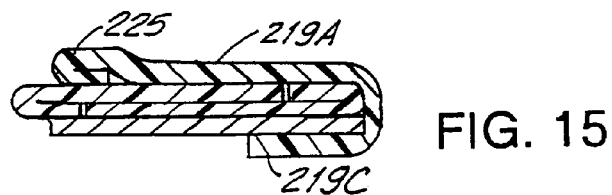
FIG. 15 is a sectional view taken along the lines 15-15 of FIG. 12.

The second embodiment of the present invention defines of multi-layer tape tabs and landing zone shown in FIGS. 12-15 which is similar to the first embodiment illustrated in FIGS. 6-9 except for differences in the fastener 219 discussed below. As shown in FIG. 12 the T-shaped 200 comprise a chassis having opposed lateral segments or wing 209,211. The construction of the diaper is otherwise the same as in FIG. 6. The fastener 219, however, consists of two layers of tapes 219A, 219C. Initially, the layer 219A is used to fasten the tape 219 to the diaper. In order to readjust the diaper, the layer 219C may be peeled off, leaving the layer 219A in place to act as a landing zone for readjustment of the diaper when necessary. After readjusting the diaper, the layer 219C is attached back onto layer 219A. Thus, the second fastening system requires less landing zone than the first embodiment while still realizing the advantage of repeated readjustment of the diaper and repositioning of the tape tab without tearing the diaper fabric. The use of multi-layer tape tab according to the second embodiment, with less landing zone area, results in increased flexibility of the wing portion of the diaper, and permits the use of elasticized wings when desired, all resulting in decreased manufacturing cost of the diaper. The construction of tape tabs 215,217 may be similar to tape tab 219.

Figure 16:
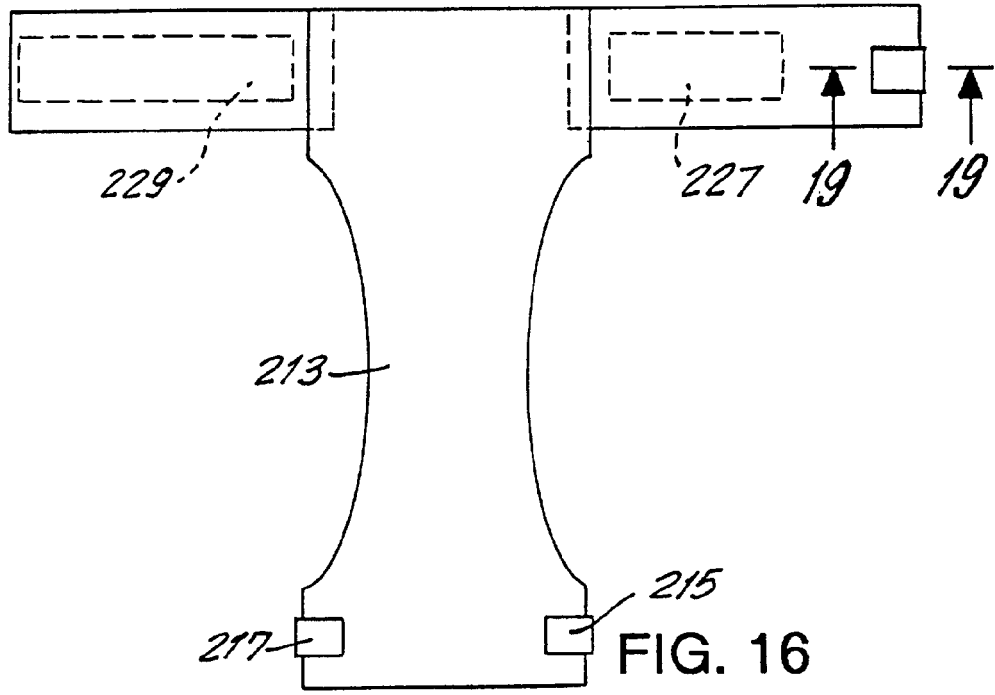
FIG. 16 is a stretched view of a T-shaped diaper similar to FIGS. 11 and 12 but employing a hook and loop fastening system according to a different embodiment of the present invention.
Figure 17:
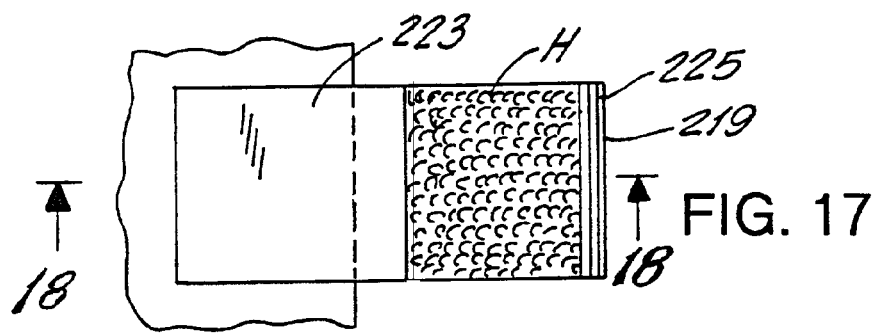
FIG. 17 is a top view of the hook system employed in FIG. 16 with the tape tab in open ready to be used position.
Figure 18:
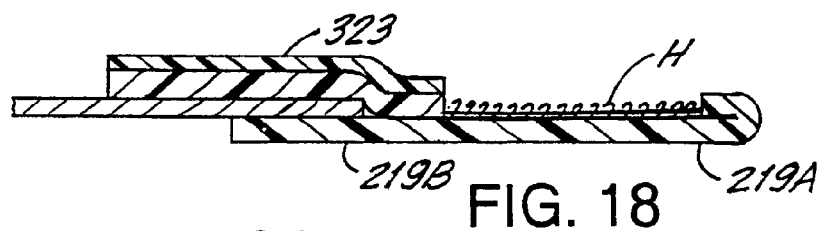
FIG. 18 is a sectional view taken along the line 18-18 of FIG. 17.
Figure 19:
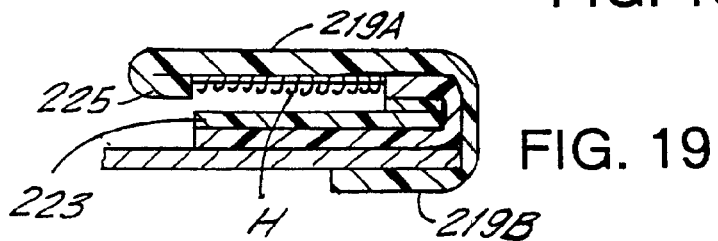
FIG. 19 is a sectional view taken along the line 19-19 in FIG. 16.

The third embodiment of the present invention employs hook and loop fastening system as illustrated in FIGS. 16-19. This fastening system is similar to the first fastening system described in connection with FIGS. 6-9 except that the landing zones 227 and 229 is covered with loop material rather than a silicone compound and the top surface of the tape portion 219A is covered with a hook material which covers the pressure sensitive adhesive. Thus, the release tab 223 covers the adhesive area that is not covered by the hook material. Referring to FIGS. 16-19, it can be seen that the configuration and construction of the T-shaped diaper of FIG. 16 is the same as in FIG. 6. Instead of being covered by a pressure sensitive adhesive as in FIG. 7, the portion 219A is covered with layer of hook material H, e.g., Velcro.RTM. A grip strip 225 facilitates gripping the end of the tape 219 when peeling the fastener.

In use, the diaper wings are wrapped as hereinbefore described, the grip strip 225 is gripped to peel the tape 219 away and expose the hook surface H and then attaching (engaging) the hook surface H onto the loop-landing zone 229 on the wing. The intersecting portion 213 is then passed under the crotch, folded thereover and the tabs 215,217 are secured to the landing zones 227,229, respectively. Again the construction of tape tabs 215,217 may be identical to tape tabs 219 in FIGS. 6, 12 and 16.

Referring to FIGS. 20-23 the fourth embodiment of the present invention is similar to the second embodiment except that the tape 219 consists of two superposed layers; a layer 219D having a top adhesive surface 219E and an opposed bottom surface 219F covered with loop material. Superposed on the tape 219D is the layer 219G which is covered with hook material H, the same as layer 219A in FIG. 18. Again tape tabs 215 and 217 may be identical to tape tab 219.

Figure 24:
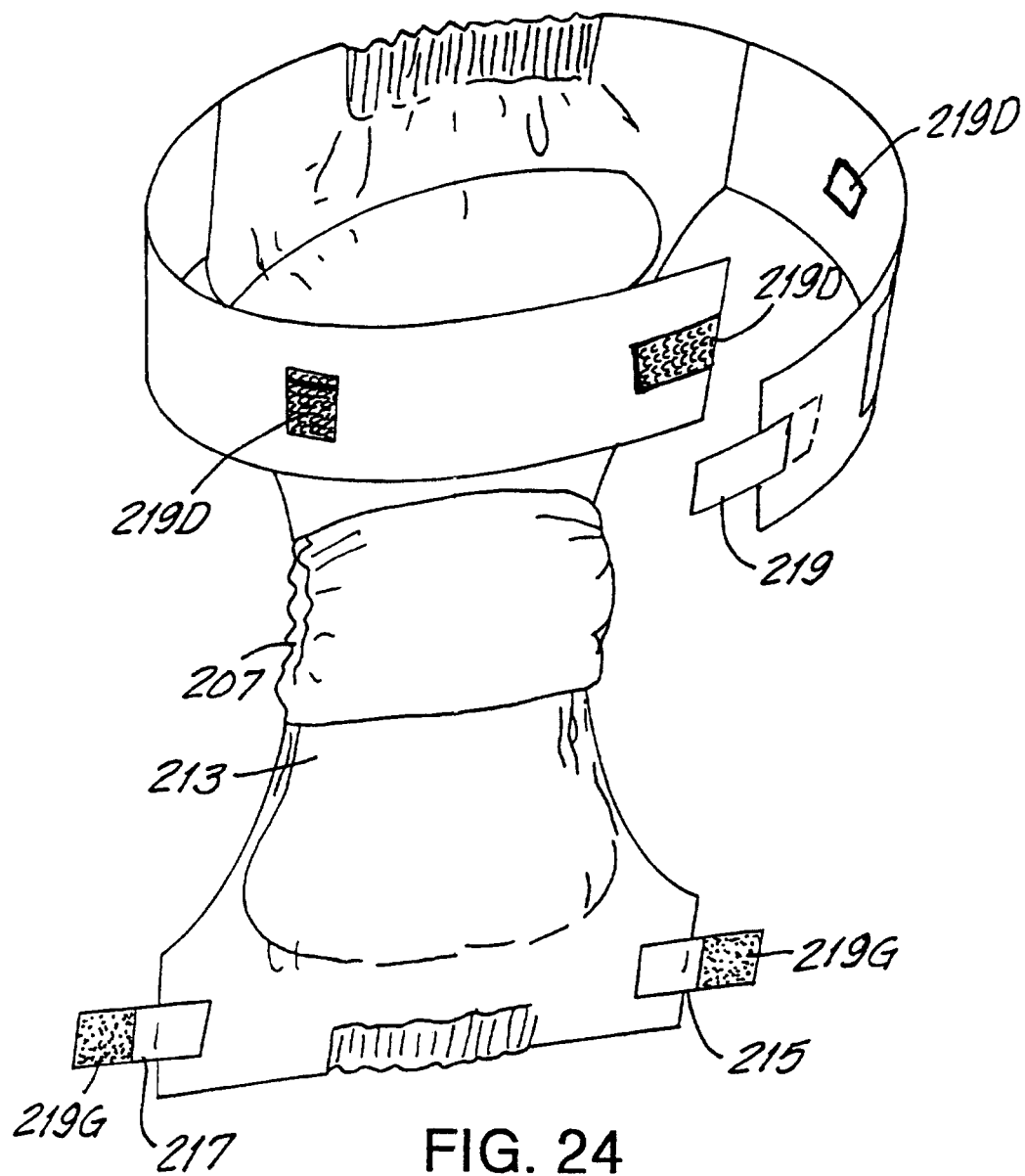
FIG. 24 is a view similar to FIG. 10 employing a multi-layer hook and loop fastening system, and illustrates the diaper after the first attempt of fastening the tape system and peeling open the diaper to show the tape tabs as in FIG. 22.

FIG. 24 illustrates a diaper, in semi-assembled position, incorporating the fastening system described in the second and fourth embodiment of the present invention. In FIG. 24, the tabs 215,217 are shown in open position after use of the diaper in order to further illustrate the fastening system. As it can be seem from this figure, after the diaper has been worn and the insert piece 213 has been removed to disassemble the diaper, there remains on the wings 227 and 229, the layers 219D as described in connection with FIG. 22.

From the foregoing detailed description it is evident that several changes and modifications may be made in the different fastening systems which are obvious from, and are suggested by the description herein. It must also be noted that the nature of the different layers, the hook and loop materials and the adhesives used are well known in the art and are mentioned in the prior art patents discussed in this application as well as the earlier related patent applications.

Figure 25:
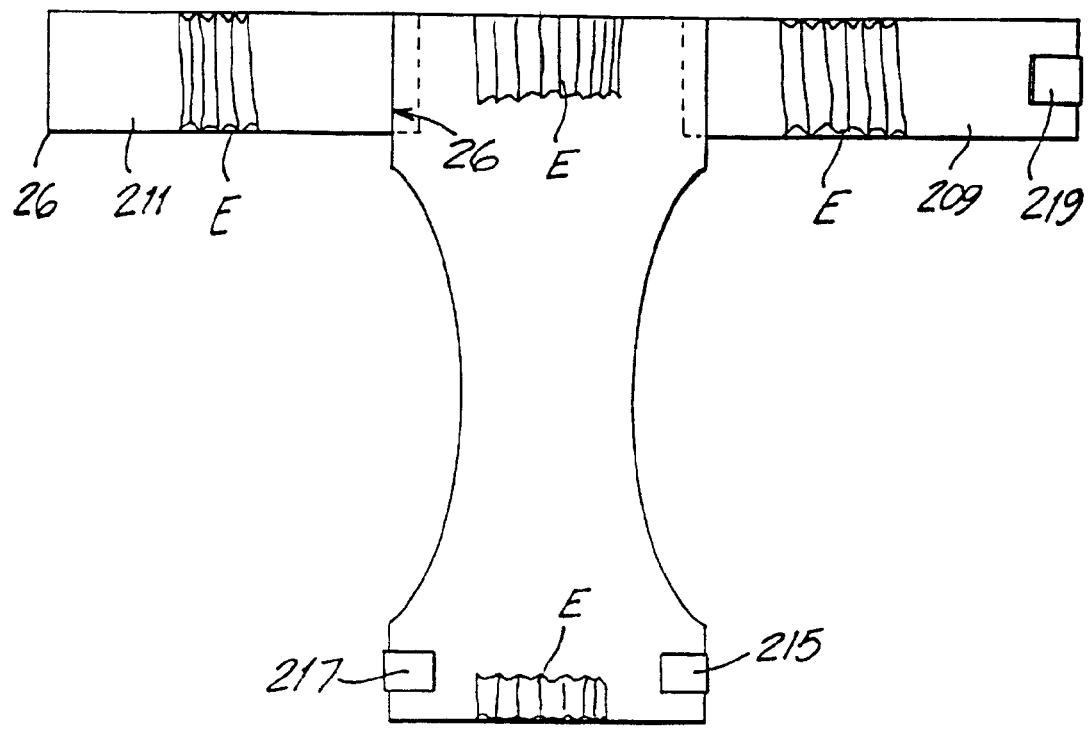
FIG. 25 is a view similar to FIG. 20 wherein the diaper is partly elasticated.
Figure 26:
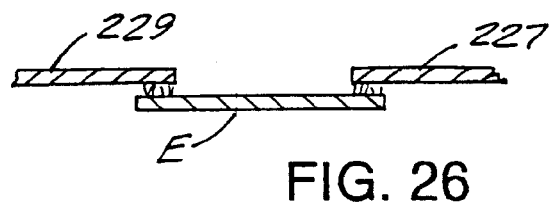
FIG. 26 is a sectional view taken along the line 26-26 of FIG. 25.
Figure 27:
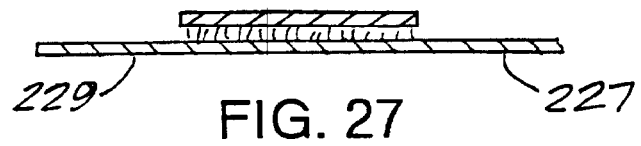
FIG. 27 is a sectional view taken along the line 27-27 of FIG. 25.

Referring to FIGS. 25-27, the diaper shown therein has elasticated portions E attached to the wings, the mid-waist section and the distal end of the insert 213 or vertical intersecting portion. The elastic material may be any of the known elastic materials used in the art. This inclusion of elastics in the aforementioned diaper portion adds to stretchability of the wings and the diaper for improved fit and comfort. Also, the wings dimension, i.e., length L and width W can vary depending on the desired size. The diaper wings are usually made from spunbond, spunbond and meltblown, thermally or chemically bonded, hydrogenated nonwoven, composites made of film and nonwoven laminates and composites made of nonwoven/film/nonwoven. The film may be elastic and the nonwoven may have 50 to 200 percent elongation capability. If desired, the composite may be apertured in order to further improve its stretchability. The wings may be added as separate pieces on each side of the chassis insert, or they can be formed as extension of the insert.

The insert 213 used in the diaper consists of a fluid permeable coversheet, a fluid impermeable backsheet and an absorbent pad sandwiched therebetween. The absorbent pad may be made of a superabsorbent polymer (SAP) of the type used in the art and wood pulp fibers having the desired density. The ratio of SAP to wood pulp may be varied over a wide range. If desired, a layer or multilayer of drylaid type material can be used as the absorbent pad, such as Rayoner Novathin 2250355 or 3400355 available from Rayonier. The front and backwaist of the insert may be elasticized by attaching elastic web between the coversheet and the backsheet of the insert front and waist area similar to the wings.

Thus, as described and shown in abandoned parent patent application Ser. No. 09/376,282 (see the paragraph bridging pages 15-16 and FIG. 28 thereof), the ear or lateral segments may be made partly or entirely from a nonwoven fabric and serve as female receiving surfaces for engagement by a male Velcro fastening means. Accordingly, no female Velcro fastening means is required on the outer surface of the ear segments since the male Velcro fastening means (whether on one of the ear segments or adjacent the outer edges of the distal end of the center piece) can be engaged onto the female receiving surface of the ear segments. The appearance of such a "loopless" embodiment of the present invention (that is, an embodiment which is devoid of female Velcro fastening means) is presented in FIG. 1 of the present application wherein the female Velcro fastening means 127, 129, 131 are not shown on either of the ear segments 117, 119 or on the distal end of the center piece 121. In this case the hook-like mini-projections of the three male Velcro fastening means 125, 137, 139 engage nonwoven outer surface portions of the ear segments 117, 119.

Figure 28:
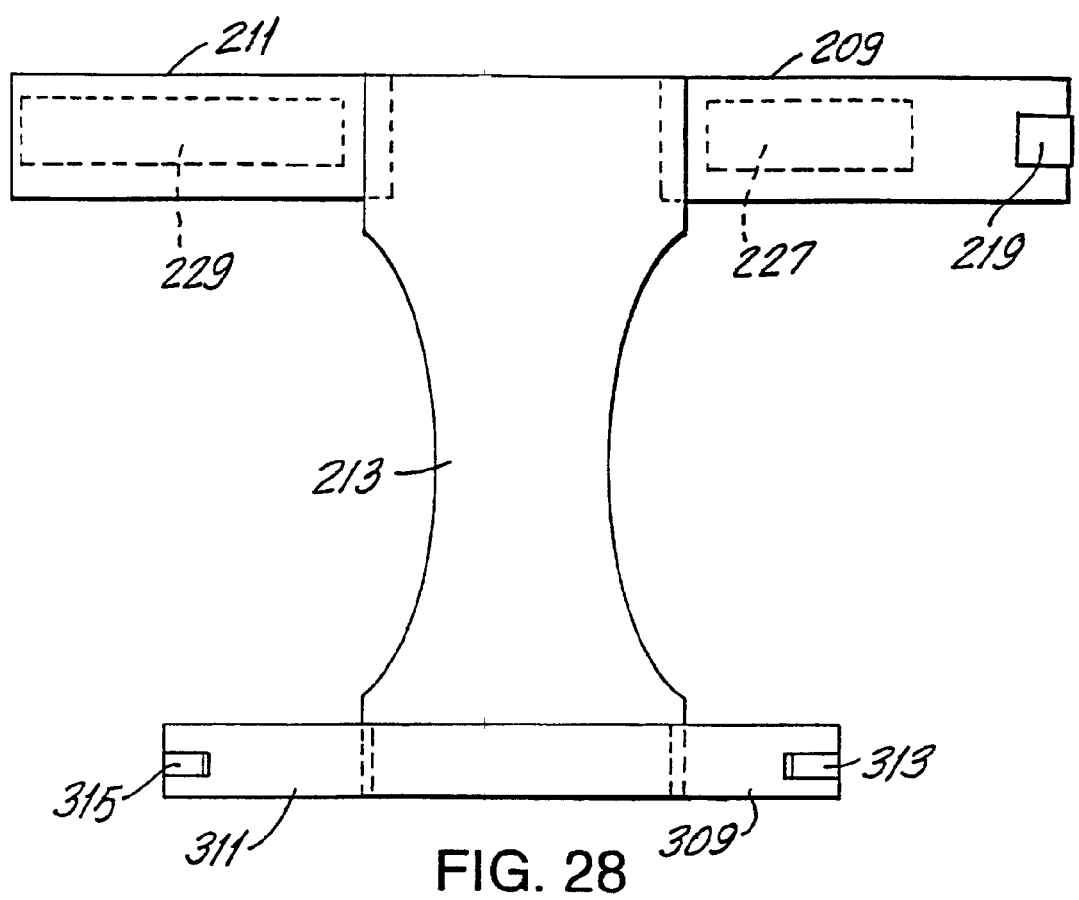
FIG. 28 is a view similar to FIG. 16 with the distal end of the vertical section having laterally extended segments or wings.

FIG. 28 illustrates an embodiment similar to the embodiment of the invention illustrated by FIG. 16. However, the embodiment shown in FIG. 28, the distal end of the vertical insert piece has lateral segments or wings 309,311. Male fastener 313,315 are located at or near the lateral ends of each of the wings 309,311.

Figure 20:
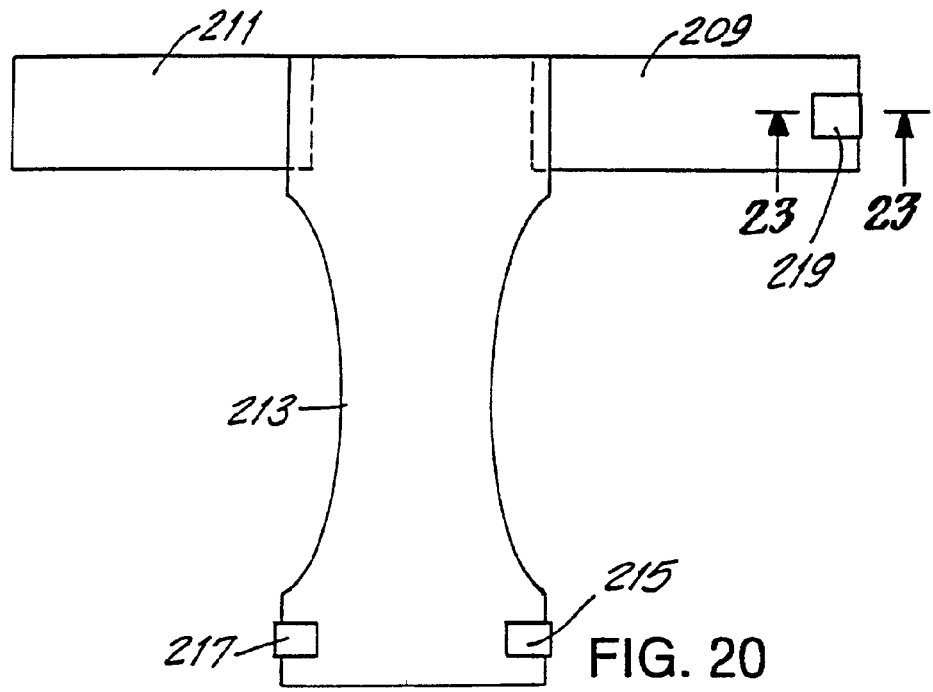
FIG. 20 is a view similar to FIG. 16 but employs a multi-layer hook and loop fastening system according to yet another embodiment of present invention.
Figure 21:
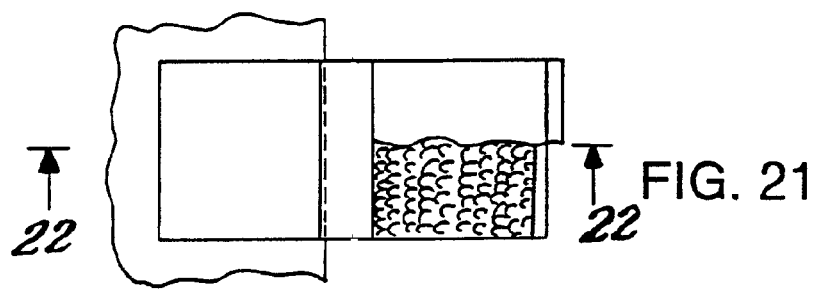
FIG. 21 is a top view of the multi-layer hook and loop fastening system used in FIG. 20 with the tape tab in open ready to be used position.
Figure 22:
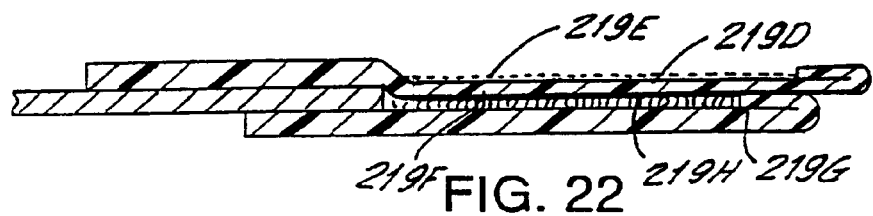
FIG. 22 is a sectional view taken along the line 22-22 in FIG. 21.
Figure 23:
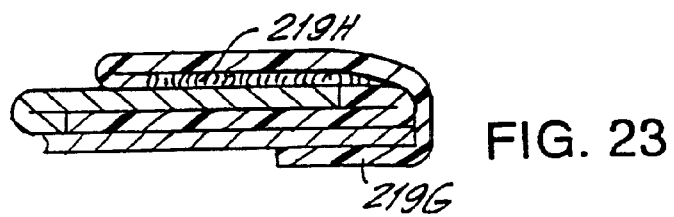
FIG. 23 is a sectional view taken along the line 23-23 in FIG. 20.
Figure 29:
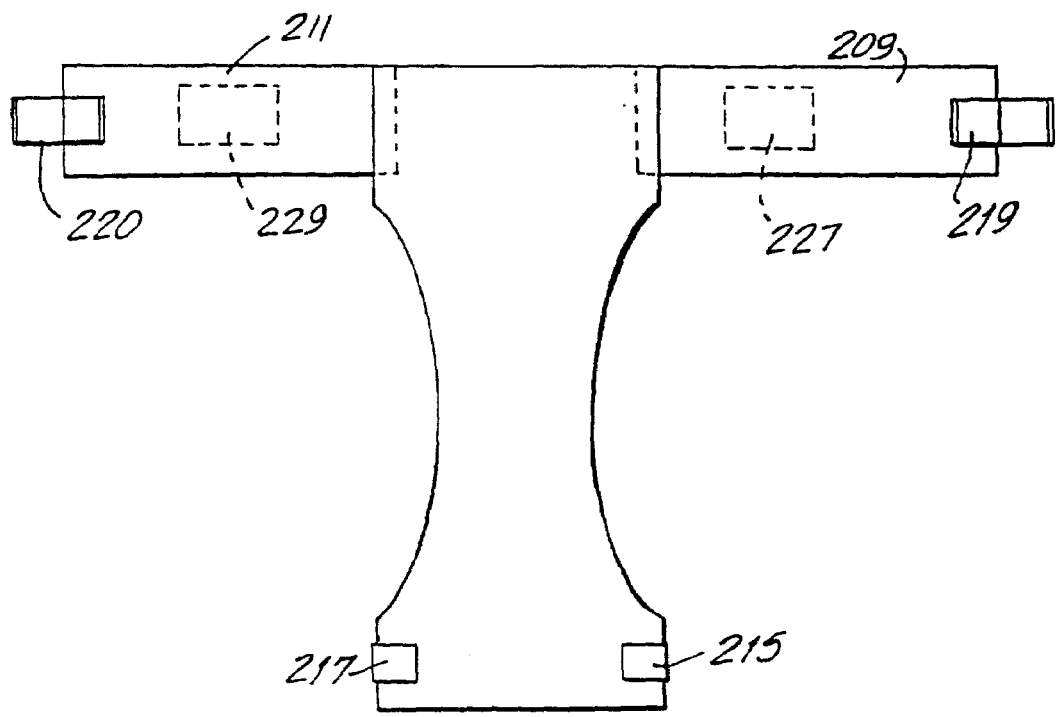
FIG. 29 is a view similar to FIG. 20 with a male fastener at one wing and a female fastener is provided at the opposite wing.
Figure 31:
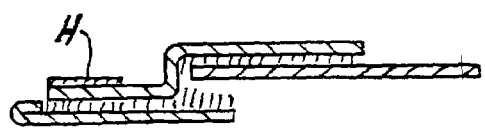
FIG. 31 is a sectional view taken along the line 31-31 of FIG. 29.
Figure 30:
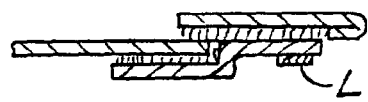
FIG. 30 is a sectional view taken along the line 30-30 of FIG. 29.
Figure 33:
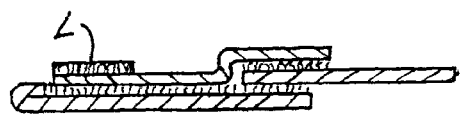
FIG. 33 is a sectional view showing the reverse position shown in FIG. 31.
Figure 32:
FIG. 32 is a sectional view showing the reverse position shown in FIG. 30.

In the diaper shown in FIG. 29, one wing has a male fastener as in FIG. 20 and the opposed lateral wing 211 has a female fastener 220. In addition, a female fastener 227,229 are attached each on the back of each wing (the side away from the skin of the wearer).

Figure 34:
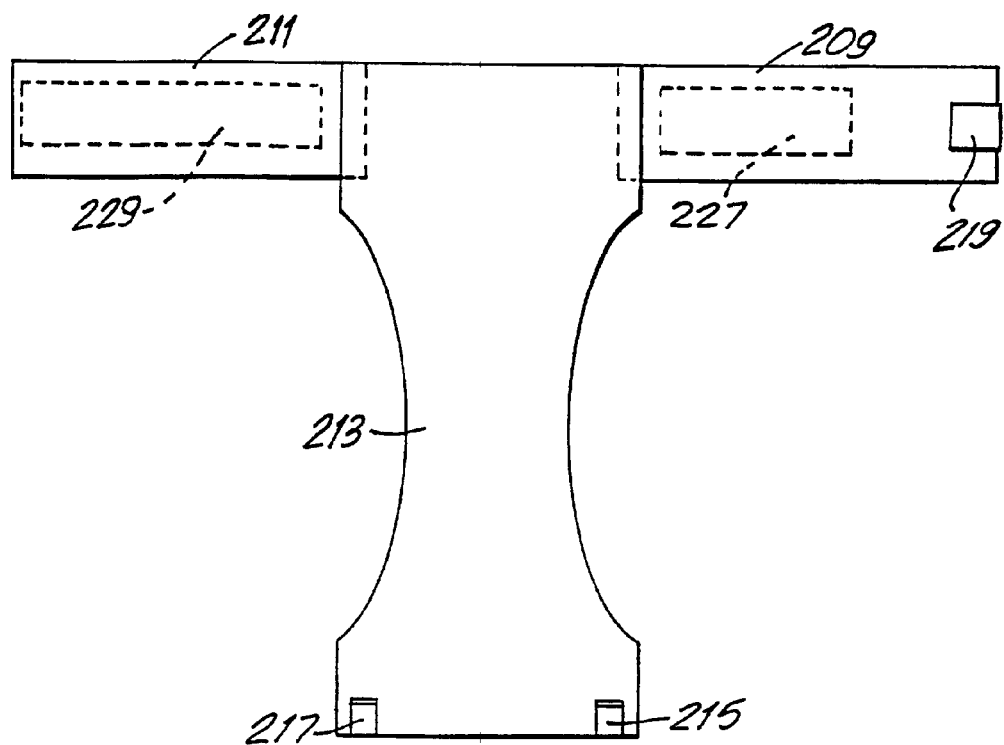
FIG. 34 is a view similar to FIG. 16 having different tape tab positions at the distal end of the vertical portion.
Figure 35:
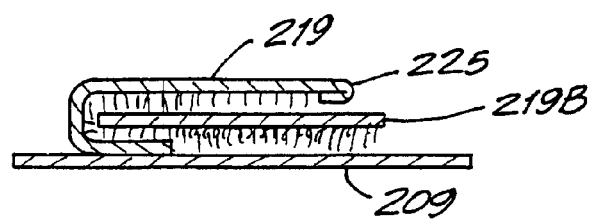
FIG. 35 is a sectional view taken along the lines 35-35 of FIG. 34.

In the diaper shown in FIG. 34, female fasteners 227,229 are attached to the back surface of the diaper wings 209,211. The tape tabs 215,217 and 219 differ from the tape tabs shown in FIGS. 6-9 in that the permanent portion 219B is eliminated in order to reduce the cost of the product (see FIG. 35, a sectional view taken along its line 35-35 of FIG. 34).

Figure 36:
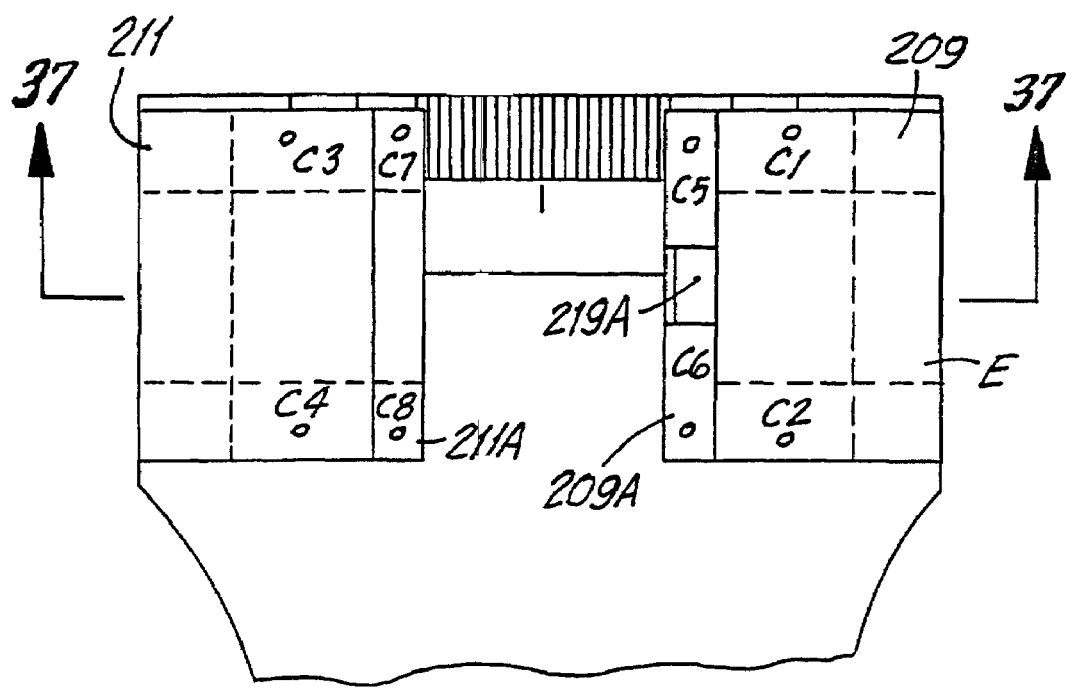
FIG. 36 is a stretched view similar to FIG. 25 wherein each wing segment is folded over itself.

In order to facilitate manufacturing and packaging the diaper, and as shown in FIG. 36, each of the lateral segments or wing 209,211 is folded upon itself toward the center of the chassis. The facing surfaces of each wing may be attached removably by a suitable adhesive, ultrasonically or by some other attachment means as indicated by dotted circles C1, C2, C3 and C4. As it can be seen from FIG. 36, each wing 209,211 also cover the insert cover sheet and is similarly attached as shown by the dotted circles C5, C6, C7 and C8. After unpacking, and in order to use the diaper, the finger lift portion 209A, 211A on each wing may be gripped between the thumb and the forefinger and the wing is lifted to an open position.

While in FIG. 36 each wing is shown folded once upon itself, as a practical matter, each wing may be folded more than once, if desired.

Figure 37:
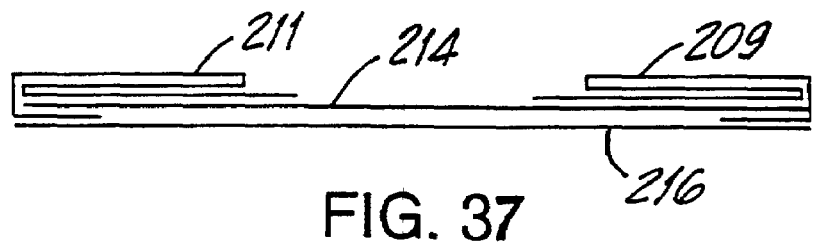
FIG. 37 is a sectional view taken along the line 37-37 of FIG. 36.

FIG. 37 shows the composition of the chassis beneath the wings 209,211 comprising a layer of nonwoven (insert coversheet) 214 and a film backing (insert backsheet) 216.

In order to further enhance the functions of and the fitness-to-wear the diaper, attention should be focused on certain relative dimensions and locations of the diaper parts as well as several other features. Both landing zones are perforated in order to facilitate breathability of the diaper. Additionally, each wing segment is made of a material, such as nonwoven, that is permeable to moisture, vapor and oxygen. The length of each landing zone is preferably equal or less than the length of the respective lateral segment on which the landing zone is located. Additionally, the width of one of the landing zones is about equal or greater than the width of the other landing zone. The landing zone on the left and right lateral segments are conveniently made at least 1 inch wide and at least about 1 inch long. Additional dimensional considerations of the landing zones play significant role in the design of a functionally effective and desirable diaper. For example, the landing zone on the left lateral segment is about 8 to about 15 inches wide and about 1 to about 7 inches long and the landing zone on the right lateral segment is about 10 to about 20 inches wide and about 1 to about 7 inches long. The distance between the outer edge of the left landing zone and the outer edge of the left lateral segment is about 6 to about 11 inches long, and the distance between the outer edge of the right landing zone and the outer edge of the right segment is from 0 to about 13 inches.

Each of the landing zones may comprise a visible indicator zone which may be in the general form of a band of about 1 to about 7 inches long generally centrally disposed on the landing zone. Each of the tape tabs can be adhered to said band in the correct diaper processing (wearing) order.

The aforementioned diapering order described herein is by way of suggestion and not intended to limit the manner which the diaper may be applied to or worn by a person. Otherwise, obvious procedures are suggested to one skilled in the art by slight and obvious modifications which are nevertheless within the scope of the present invention.

The diaper also comprises an insert as well as side cuffs, front waist cuffs, back waist cuffs and elastic waists. The construction, dimensions and relative location of these components are also important consideration in the design of a functionally effective diaper. The construction of these cuffs may be the same as conventional cuffs of the prior art diaper, but preferably these barrier cuffs are made of a layer of nonwoven similar to the diaper coversheet or a composite made from a nonwoven and a polyethylene film.

For increased fitness of the diaper, it is desirable that the center of the waistband bear a defined relationship to the center of the tape tabs. Thus, optimum fitness can be achieved when a line drawn through the center of the waistband coincides with the line drawn through the center of each tape tab, or when the distance between these center lines is between about 0 and 3 inches.

The length of the absorbent core is preferably about 30 to 80 percent of the overall width of the diaper, with the absorbent core being located about 1.5 inches from the front edge of insert. Also, the front insert width is equal to or greater than the width of the back insert, and the front insert width is equal to or less than the overall width of the diaper.

In order to make the diaper user friendly each of the two tape tabs attached to the insert has a numerical indicia such a the number 2 on the left side and the number 3 on the right side, or vice versa. In addition, the tapes on the ear segment and the tapes on the insert are also provided with numerical indicia such as the number 1. These digits indicate and facilitate the diapering process. More than one of each indicia may be printed on each tab to assure that at least one indicia on each tab remains visible during the application of the diaper.

Regarding the width of the diaper, it is preferable that the relaxed width of the diaper (in its normal unstretched position) be between about 20 to about 100 percent of the width B of the diaper in its fully stretched position. This assures tight fit of the diaper to the torso of the wearer.

The dimensions of the second portion of the diaper are also significant design considerations. Thus, the second portion has a front width which is at least about 10 inches, preferably about 15 to about 25 inches, and the width is equal or less than the width of the back of said second portion. Moreover, the length of the second portion is about equal or less than the overall width of the chassis.

Each of the lateral segments of the absorbent article is desirably from about 2 to about 15 inches long and from about 10 to about 30 inches wide.

The width of the insert is from about 8 to about 40 percent of said width when fully stretched and the relaxed width of said second portion is from about 10 to about 100 percent of said width when fully stretched.

The materials used for making the diaper are generally well known in the art and are described in the aforementioned parent applications and the prior art patents cited therein. In this connection, the length of the absorbent core or layer is about 20 to about 40 inches and contains up to about 60 weight percent superabsorbent polymer (SAP) and up to about 40 weight percent by weight of hydrophilic fibers of the type known and described in the prior art.

Additional design modifications further enhance the effective use of the diaper. Thus, referring to FIG. 29, when wearing the diaper, tape tab 219 may be fastened to the tape tab 215, and tape tab 220 may be fastened to tape tab 217. Also, while FIG. 28 shows that the diaper is provided with front wings or segments 209,211, if desired, the diaper may be provided with rear segments as well (not shown). Additionally, and referring to FIGS. 25, 26 and 27, while the diaper is shown with one elastic zone, it may be provided with more than one elastic zone, preferably three elastic zones. Furthermore, referring to FIG. 35, the crotch cuffs may be folded inwardly or outwardly and secured together by a suitable adhesive, approximately 2 inches from each corner.

The foregoing description of the relative dimensions and other features of the diaper are significant in the manufacture of a commercially acceptable and functionally effective diaper. Other changes and modifications become obvious from the description herein.

The invention claimed is:

1. A disposable absorbent article comprising:
a chassis formed of two portions, a first portion and a second portion which together define a generally T-shaped configuration when the chassis is viewed in a stretched position, the first portion having opposed lateral segments adapted to be wrapped around the waist of a wearer of the article and overlap each other, each of the lateral segments having an outer edge and a nonwoven outer surface, and the second portion having a proximal end and a distal end having opposed lateral sides disposed generally vertically relative to the first portion and adapted to be passed under the crotch of the wearer and folded upwardly and over the overlapped opposed lateral segments of the first portion;

one male fastening means on an inner surface of one of the lateral segments adjacent the outer edge thereof, such that, when the lateral segments overlap each other, the one male fastening means engages an outer surface portion of the other lateral segment; and a pair of opposed spaced apart male fastening means on an inner surface of the distal end of the second portion, each adjacent a respective one of the lateral sides thereof, such that, when the lateral segments are wrapped around the waist of a wearer and the second portion is folded over the lateral segments, each one of the pair of male fastening means engages a correspondingly aligned outer surface portion of a respective lateral segment, such that the article has a total of only three male fastening means, each of the three male fastening means comprising a first tape tab layer and a second tape tab layer, each of the first and second tape tab layers defining hook-like mini-projections for direct engagement with the nonwoven outer surfaces of the lateral segments, the first tape tab layer being disposed directly adjacent to a respective one of the outer nonwoven surfaces, and the second tape tab layer being disposed over the first tape tab layer, the second tape tab layer being removeably attached to the first tape tab layer so that a position of the second tape tab layer is adjustable with respect to the first tape tab layer and the respective outer nonwoven surface, wherein each of the lateral segments is laterally folded over on itself at least once, with at least a pair of facing surfaces thereof releasably secured together, prior to use thereof.

2. The disposable absorbent article of claim 1, wherein each of the lateral segments are made of a nonwoven material including at least one elastic portion.

3. The disposable absorbent article of claim 1, wherein the three male fastening means are provided with numerical indicia that define the order of wearing the article.

\* \* \* \* \*